(12) United States Patent
Hill et al.

(10) Patent No.: US 8,292,918 B2
(45) Date of Patent: Oct. 23, 2012

(54) COMPOSITE PLUG FOR ARTERIOTOMY CLOSURE AND METHOD OF USE

(75) Inventors: Jason P. Hill, Brooklyn Park, MN (US); Susan M. Shoemaker, Elk River, MN (US); James G. Hansen, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 583 days.

(21) Appl. No.: 12/390,289

(22) Filed: Feb. 20, 2009

(65) Prior Publication Data

US 2010/0217312 A1    Aug. 26, 2010

(51) Int. Cl.
*A61B 17/08*    (2006.01)

(52) U.S. Cl. .................................. 606/213

(58) Field of Classification Search ............ 606/213, 606/95; 623/23.48; 604/15, 60, 57; 128/887
See application file for complete search history.

(56) References Cited

U.S. PATENT DOCUMENTS

| | | | |
|---|---|---|---|
| 3,952,377 A * | 4/1976 | Morell | 24/136 R |
| 5,021,059 A | 6/1991 | Kensey et al. | |
| 5,061,274 A * | 10/1991 | Kensey | 606/213 |
| 5,084,050 A * | 1/1992 | Draenert | 606/77 |
| 5,108,421 A | 4/1992 | Fowler | |
| 5,129,882 A | 7/1992 | Weldon et al. | |
| 5,192,300 A | 3/1993 | Fowler | |
| 5,192,302 A | 3/1993 | Kensey et al. | |
| 5,221,259 A | 6/1993 | Weldon et al. | |
| 5,222,974 A | 6/1993 | Kensey et al. | |
| 5,254,105 A | 10/1993 | Haaga | |
| 5,275,616 A | 1/1994 | Fowler | |
| 5,282,827 A | 2/1994 | Kensey et al. | |
| 5,290,310 A | 3/1994 | Makower et al. | |
| 5,292,332 A | 3/1994 | Lee | |
| 5,310,407 A | 5/1994 | Casale | |
| 5,312,435 A | 5/1994 | Nash et al. | |
| 5,320,639 A | 6/1994 | Rudnick | |
| 5,334,216 A * | 8/1994 | Vidal et al. | 606/213 |
| 5,342,393 A | 8/1994 | Stack | |
| 5,350,399 A | 9/1994 | Erlebacher et al. | |
| 5,370,660 A | 12/1994 | Weinstein et al. | |
| 5,383,896 A | 1/1995 | Gershony et al. | |
| 5,383,899 A | 1/1995 | Hammerslag | |
| 5,383,905 A * | 1/1995 | Golds et al. | 606/232 |
| 5,391,183 A | 2/1995 | Janzen et al. | |
| 5,411,520 A | 5/1995 | Nash et al. | |
| 5,413,571 A | 5/1995 | Katsaros et al. | |

(Continued)

FOREIGN PATENT DOCUMENTS

EP    1568326 A1    8/2005

(Continued)

*Primary Examiner* — Julian Woo
*Assistant Examiner* — Christopher L Templeton
(74) *Attorney, Agent, or Firm* — Seager, Tufte & Wickhem LLC

(57) ABSTRACT

A composite plug for arteriotomy closure, a method of manufacturing a composite plug for arteriotomy closure, and a method for the use of a composite plug for arteriotomy closure may include an elongate core member, and one or more layers disposed at least in part about the core member, where the composite plug has been partially compacted in a radial direction. The composite plug may include an outer member at least partially surrounding the core member.

20 Claims, 4 Drawing Sheets

U.S. PATENT DOCUMENTS

| | | | |
|---|---|---|---|
| 5,415,657 A | 5/1995 | Taymor-Luria | |
| 5,419,765 A | 5/1995 | Weldon et al. | |
| 5,437,631 A | 8/1995 | Janzen | |
| 5,441,517 A | 8/1995 | Kensey et al. | |
| 5,443,481 A | 8/1995 | Lee | |
| 5,447,502 A | 9/1995 | Haaga | |
| 5,454,833 A | 10/1995 | Boussignac et al. | |
| 5,478,326 A | 12/1995 | Shiu | |
| 5,478,352 A | 12/1995 | Fowler | |
| 5,486,195 A | 1/1996 | Myers et al. | |
| 5,529,577 A | 6/1996 | Hammerslag | |
| 5,531,759 A | 7/1996 | Kensey et al. | |
| 5,540,715 A | 7/1996 | Katsaros et al. | |
| 5,545,178 A | 8/1996 | Kensey et al. | |
| 5,549,633 A | 8/1996 | Evans et al. | |
| 5,571,181 A | 11/1996 | Li | |
| 5,573,518 A | 11/1996 | Haaga | |
| 5,591,204 A | 1/1997 | Janzen et al. | |
| 5,593,422 A | 1/1997 | Muijs Van de Moer et al. | |
| 5,601,602 A | 2/1997 | Fowler | |
| 5,613,974 A | 3/1997 | Andreas et al. | |
| 5,620,461 A | 4/1997 | Muijs Van De Moer et al. | |
| 5,626,601 A | 5/1997 | Gershony et al. | |
| 5,630,833 A | 5/1997 | Katsaros et al. | |
| 5,649,959 A | 7/1997 | Hannam et al. | |
| 5,653,730 A | 8/1997 | Hammerslag | |
| 5,662,681 A | 9/1997 | Nash et al. | |
| 5,676,689 A | 10/1997 | Kensey et al. | |
| 5,700,277 A | 12/1997 | Nash et al. | |
| 5,702,421 A * | 12/1997 | Schneidt | 606/213 |
| 5,707,393 A | 1/1998 | Kensey et al. | |
| 5,716,375 A | 2/1998 | Fowler | |
| 5,725,498 A | 3/1998 | Janzen et al. | |
| 5,725,551 A | 3/1998 | Myers et al. | |
| 5,728,114 A | 3/1998 | Evans et al. | |
| 5,728,122 A | 3/1998 | Leschinsky et al. | |
| 5,728,133 A | 3/1998 | Kontos | |
| 5,728,134 A | 3/1998 | Barak | |
| 5,741,223 A | 4/1998 | Janzen et al. | |
| 5,782,860 A | 7/1998 | Epstein et al. | |
| 5,810,884 A | 9/1998 | Kim | |
| 5,830,130 A | 11/1998 | Janzen et al. | |
| 5,843,124 A | 12/1998 | Hammerslag | |
| 5,853,421 A | 12/1998 | Leschinsky et al. | |
| 5,861,004 A | 1/1999 | Kensey et al. | |
| 5,871,474 A | 2/1999 | Hermann et al. | |
| 5,871,501 A | 2/1999 | Leschinsky et al. | |
| 5,906,631 A | 5/1999 | Imran | |
| 5,916,236 A | 6/1999 | Muijs Van de Moer et al. | |
| 5,922,009 A | 7/1999 | Epstein et al. | |
| 5,935,147 A | 8/1999 | Kensey et al. | |
| 5,935,169 A * | 8/1999 | Chan | 623/23.48 |
| 5,947,997 A | 9/1999 | Pavcnik et al. | |
| 5,948,425 A | 9/1999 | Janzen et al. | |
| 5,951,583 A | 9/1999 | Jensen et al. | |
| 5,957,952 A | 9/1999 | Gershony et al. | |
| 6,007,561 A | 12/1999 | Bourque et al. | |
| 6,017,359 A | 1/2000 | Gershony et al. | |
| 6,045,569 A | 4/2000 | Kensey et al. | |
| 6,045,570 A | 4/2000 | Epstein et al. | |
| 6,048,357 A | 4/2000 | Kontos | |
| 6,048,358 A | 4/2000 | Barak | |
| 6,054,569 A | 4/2000 | Bennett et al. | |
| 6,056,768 A | 5/2000 | Cates et al. | |
| 6,056,769 A | 5/2000 | Epstein et al. | |
| 6,056,770 A | 5/2000 | Epstein et al. | |
| 6,080,183 A | 6/2000 | Tsugita et al. | |
| 6,083,522 A * | 7/2000 | Chu et al. | 424/423 |
| 6,110,184 A | 8/2000 | Weadock | |
| 6,120,524 A | 9/2000 | Taheri | |
| 6,126,675 A | 10/2000 | Shchervinsky et al. | |
| 6,162,240 A | 12/2000 | Cates et al. | |
| 6,179,863 B1 | 1/2001 | Kensey et al. | |
| 6,183,496 B1 | 2/2001 | Urbanski | |
| 6,190,400 B1 | 2/2001 | Van De Moer et al. | |
| 6,200,329 B1 * | 3/2001 | Fung et al. | 606/232 |
| 6,251,141 B1 * | 6/2001 | Pierson et al. | 623/23.48 |
| 6,261,309 B1 | 7/2001 | Urbanski | |
| 6,296,632 B1 | 10/2001 | Luscher et al. | |
| 6,296,657 B1 | 10/2001 | Brucker | |
| 6,296,658 B1 | 10/2001 | Gershony et al. | |
| 6,325,789 B1 | 12/2001 | Janzen et al. | |
| 6,350,274 B1 | 2/2002 | Li | |
| 6,368,300 B1 | 4/2002 | Fallon et al. | |
| 6,368,341 B1 | 4/2002 | Abrahamson | |
| 6,425,911 B1 | 7/2002 | Akerfeldt et al. | |
| 6,461,346 B1 | 10/2002 | Buelna | |
| 6,464,712 B1 | 10/2002 | Epstein et al. | |
| 6,468,293 B2 | 10/2002 | Bonutti et al. | |
| 6,475,177 B1 | 11/2002 | Suzuki | |
| 6,475,230 B1 | 11/2002 | Bonutti et al. | |
| 6,500,152 B1 | 12/2002 | Illi | |
| 6,508,828 B1 | 1/2003 | Akerfeldt et al. | |
| 6,524,328 B2 | 2/2003 | Levinson | |
| 6,527,734 B2 | 3/2003 | Cragg et al. | |
| 6,537,299 B1 | 3/2003 | Hogendijk et al. | |
| 6,540,735 B1 | 4/2003 | Ashby et al. | |
| 6,569,187 B1 | 5/2003 | Bonutti et al. | |
| 6,572,635 B1 | 6/2003 | Bonutti | |
| 6,592,608 B2 | 7/2003 | Fisher et al. | |
| 6,596,012 B2 | 7/2003 | Akerfeldt et al. | |
| 6,596,014 B2 | 7/2003 | Levinson et al. | |
| 6,613,070 B2 | 9/2003 | Redmond et al. | |
| 6,623,509 B2 | 9/2003 | Ginn | |
| 6,632,238 B2 | 10/2003 | Ginn et al. | |
| 6,645,225 B1 * | 11/2003 | Atkinson | 606/213 |
| 6,656,207 B2 | 12/2003 | Epstein et al. | |
| 6,663,655 B2 | 12/2003 | Ginn et al. | |
| 6,682,489 B2 | 1/2004 | Tenerz et al. | |
| 6,685,727 B2 | 2/2004 | Fisher et al. | |
| 6,699,261 B1 | 3/2004 | Cates et al. | |
| 6,712,837 B2 | 3/2004 | Åkerfeldt et al. | |
| 6,733,515 B1 | 5/2004 | Edwards et al. | |
| 6,743,195 B2 | 6/2004 | Zucker | |
| 6,749,621 B2 | 6/2004 | Pantages et al. | |
| 6,764,500 B1 | 7/2004 | Muijs Van De Moer et al. | |
| 6,780,197 B2 | 8/2004 | Roe et al. | |
| 6,790,220 B2 | 9/2004 | Morris et al. | |
| 6,818,008 B1 | 11/2004 | Cates et al. | |
| 6,860,895 B1 | 3/2005 | Akerfeldt et al. | |
| 6,863,680 B2 | 3/2005 | Ashby | |
| 6,890,342 B2 | 5/2005 | Zhu et al. | |
| 6,890,343 B2 | 5/2005 | Ginn et al. | |
| 6,896,692 B2 | 5/2005 | Ginn et al. | |
| 6,929,655 B2 | 8/2005 | Egnelov et al. | |
| 6,939,363 B2 | 9/2005 | Åkerfeldt | |
| 6,942,684 B2 | 9/2005 | Bonutti | |
| 6,955,683 B2 | 10/2005 | Bonutti | |
| 6,964,658 B2 | 11/2005 | Ashby et al. | |
| 6,969,397 B2 | 11/2005 | Ginn | |
| 7,001,398 B2 | 2/2006 | Carley et al. | |
| 7,008,439 B1 | 3/2006 | Janzen et al. | |
| 7,008,440 B2 | 3/2006 | Sing et al. | |
| 7,008,441 B2 | 3/2006 | Zucker | |
| 7,008,442 B2 | 3/2006 | Brightbill | |
| 7,025,776 B1 | 4/2006 | Houser et al. | |
| 7,037,323 B2 | 5/2006 | Sing et al. | |
| 7,044,916 B2 | 5/2006 | Tenerz et al. | |
| 7,083,635 B2 | 8/2006 | Ginn | |
| 7,192,436 B2 | 3/2007 | Sing et al. | |
| 7,267,679 B2 | 9/2007 | McGuckin, Jr. et al. | |
| 7,316,704 B2 | 1/2008 | Bagaoisan et al. | |
| 7,322,976 B2 | 1/2008 | Yassinzadeh | |
| 7,331,979 B2 | 2/2008 | Khosravi et al. | |
| 7,331,981 B2 | 2/2008 | Cates et al. | |
| 7,335,220 B2 | 2/2008 | Khosravi et al. | |
| 7,488,340 B2 * | 2/2009 | Kauphusman et al. | 606/213 |
| 7,491,217 B1 * | 2/2009 | Hendren et al. | 606/232 |
| 7,695,492 B1 * | 4/2010 | Ashby et al. | 606/213 |
| 7,749,279 B2 * | 7/2010 | Twomey et al. | 623/23.48 |
| 2002/0002889 A1 | 1/2002 | Ashby et al. | |
| 2002/0016612 A1 | 2/2002 | Ashby et al. | |
| 2002/0198562 A1 | 12/2002 | Akerfeldt et al. | |
| 2003/0023267 A1 * | 1/2003 | Ginn | 606/213 |
| 2003/0051735 A1 * | 3/2003 | Pavcnik et al. | 128/831 |
| 2003/0088271 A1 | 5/2003 | Cragg et al. | |
| 2004/0093025 A1 | 5/2004 | Egnelov | |

| | | |
|---|---|---|
| 2004/0098044 A1 | 5/2004 | Van de Moer et al. |
| 2004/0098046 A1 | 5/2004 | Tenerz et al. |
| 2004/0158287 A1* | 8/2004 | Cragg et al. .................. 606/213 |
| 2004/0172059 A1 | 9/2004 | Tenerz et al. |
| 2004/0204741 A1 | 10/2004 | Egnelov et al. |
| 2004/0215232 A1 | 10/2004 | Belhe et al. |
| 2004/0243007 A1 | 12/2004 | Tenerz et al. |
| 2005/0033360 A1* | 2/2005 | Sing et al. .................... 606/213 |
| 2005/0049637 A1 | 3/2005 | Morris et al. |
| 2005/0085852 A1 | 4/2005 | Ditter |
| 2005/0085855 A1 | 4/2005 | Forsberg |
| 2005/0096696 A1 | 5/2005 | Forsberg |
| 2005/0096697 A1 | 5/2005 | Forsberg et al. |
| 2005/0107827 A1 | 5/2005 | Paprocki |
| 2005/0125031 A1 | 6/2005 | Pipenhagen et al. |
| 2005/0137624 A1 | 6/2005 | Fallman |
| 2005/0169974 A1 | 8/2005 | Tenerz et al. |
| 2005/0177189 A1 | 8/2005 | Ginn et al. |
| 2005/0267521 A1 | 12/2005 | Forsberg |
| 2005/0267528 A1* | 12/2005 | Ginn et al. .................... 606/214 |
| 2006/0004408 A1 | 1/2006 | Morris et al. |
| 2006/0030886 A1 | 2/2006 | Clark |
| 2006/0034930 A1* | 2/2006 | Khosravi et al. .............. 424/484 |
| 2006/0047313 A1 | 3/2006 | Khanna et al. |
| 2006/0058844 A1 | 3/2006 | White et al. |
| 2006/0100664 A1 | 5/2006 | Pai et al. |
| 2006/0135996 A1* | 6/2006 | Schwartz et al. ............. 606/232 |
| 2006/0142797 A1 | 6/2006 | Egnelov |
| 2006/0173492 A1 | 8/2006 | Akerfeldt et al. |
| 2006/0178682 A1 | 8/2006 | Boehlke |
| 2006/0206146 A1 | 9/2006 | Tenerz |
| 2006/0229669 A1* | 10/2006 | Mirizzi et al. ................ 606/213 |
| 2006/0229672 A1 | 10/2006 | Forsberg |
| 2006/0229673 A1 | 10/2006 | Forsberg |
| 2006/0229674 A1 | 10/2006 | Forsberg |
| 2006/0265006 A1 | 11/2006 | White et al. |
| 2006/0265007 A1 | 11/2006 | White et al. |
| 2006/0265008 A1 | 11/2006 | Maruyama et al. |
| 2006/0276871 A1* | 12/2006 | Lamson et al. ............... 623/1.11 |
| 2007/0032823 A1 | 2/2007 | Tegg |
| 2007/0032824 A1 | 2/2007 | Terwey |
| 2007/0038244 A1 | 2/2007 | Morris et al. |
| 2007/0038245 A1 | 2/2007 | Morris et al. |
| 2007/0073337 A1* | 3/2007 | Abbott et al. .................. 606/213 |
| 2007/0073345 A1 | 3/2007 | Pipenhagen et al. |
| 2007/0083231 A1 | 4/2007 | Lee |
| 2007/0083232 A1 | 4/2007 | Lee |
| 2007/0129757 A1* | 6/2007 | Armstrong .................... 606/213 |
| 2007/0135842 A1 | 6/2007 | Van de Moer et al. |
| 2007/0276433 A1 | 11/2007 | Huss |
| 2008/0004657 A1* | 1/2008 | Obermiller et al. ........... 606/213 |
| 2008/0065121 A1 | 3/2008 | Kawaura et al. |
| 2008/0071311 A1 | 3/2008 | White et al. |
| 2008/0097521 A1 | 4/2008 | Khosravi et al. |
| 2008/0109030 A1 | 5/2008 | Houser et al. |
| 2008/0114394 A1 | 5/2008 | Houser et al. |
| 2009/0024106 A1 | 1/2009 | Morris |
| 2009/0069843 A1* | 3/2009 | Agnew .......................... 606/213 |
| 2009/0118757 A1* | 5/2009 | Burnett et al. ................ 606/192 |
| 2009/0171388 A1* | 7/2009 | Dave et al. .................... 606/213 |

FOREIGN PATENT DOCUMENTS

| | | |
|---|---|---|
| EP | 1671591 A1 | 6/2006 |
| WO | 8911301 A1 | 11/1989 |
| WO | 2006078578 A2 | 7/2006 |
| WO | 2006124238 A2 | 11/2006 |

* cited by examiner

COMPOSITE PLUG FOR ARTERIOTOMY CLOSURE AND METHOD OF USE

BACKGROUND OF THE INVENTION

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. Further, external pressure to close the vascular puncture site works best when the vessel is close to the skin surface but may be unsuitable for patients with substantial amounts of subcutaneous adipose tissue since the skin surface may be a considerable distance from the vascular puncture site.

There are several approaches to close the vascular puncture site including the use of anchor and plug systems as well as suture systems. Internal suturing of the blood vessel puncture requires a specialty designed suturing device. These suturing devices involve a significant number of steps to perform suturing and require substantial expertise. Additionally, when releasing hemostasis material at the puncture site and withdrawing other devices out of the tissue tract, the currently employed approaches to sealing the puncture may only partially occlude the tract thereby allowing blood to seep out of the puncture.

SUMMARY

The disclosure pertains to a composite plug for arteriotomy closure comprising an elongate core member having a distal end, a proximal end, and a lumen connecting the distal end and the proximal end, said lumen sized to receive a suture, and one or more layers disposed at least in part about the plug, wherein the core member comprises a gelatin foam and the one or more layers which may include a hydrogel and/or a hemostatic material, further wherein the plug has been partially compacted in a radial dimension.

In another aspect, the disclosure pertains to a method of manufacturing a composite plug for arteriotomy closure comprising the steps of providing a gelatin foam blank larger than a desired core member; removing excess gelatin foam from the gelatin foam blank larger than a desired core member to form a core member having a distal end and a proximal end; providing a lumen sized to receive a suture, said lumen connecting the distal end and the proximal end of core member; providing at least one layer disposed about the plug, which said layer may include a hydrogel and/or a hemostatic material; providing a suture within the lumen which extends distally and proximately from the core member; and partially compacting the plug in a radial dimension.

In yet another aspect, the disclosure pertains to a method of deploying a composite plug for arteriotomy closure comprising the steps of providing a composite plug comprising an elongate core member having a distal end, a proximal end, and a lumen connecting the distal end and the proximal end, said lumen sized to receive a suture and one or more layers disposed at least in part about the plug, wherein the core member comprises a gelatin foam and one or more layers comprising a material which may include a hydrogel and/or a hemostatic material, further wherein the plug includes a suture extending through the lumen; radially compacting the plug; inserting the compacted plug into a temporary containment sheath; providing an anchoring site adjacent to a vessel; attaching the suture to the anchoring site; inserting the temporary containment sheath at least partially into a tract adjacent to the vessel; ejecting the composite plug from the temporary containment sheath; and positioning the composite plug adjacent to the vessel and within the tract.

It is within the scope of the disclosure to include within the arteriotomy closure plug an outer member which at least partially surrounds the core member as well as additional layers which may include a hydrogel and/or a hemostatic material applied to the outer member.

DETAILED DESCRIPTION

Figure 1B:
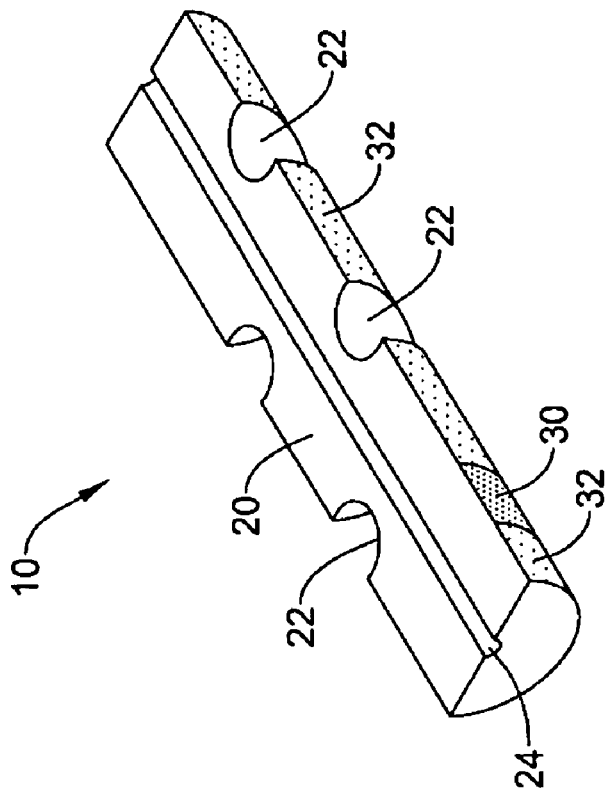
FIG. 1B is a perspective view of a longitudinally sectioned composite arteriotomy closure plug of FIG. 1A.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

Embodiments are described herein in the context of a hemostatic pressure plug. Those of ordinary skill in the art will appreciate that the following detailed description is illustrative only and is not intended to be in any way limiting. In the interest of clarity, not all of the routine features of the implementations described herein are shown and described.

Providing hemostasis at a blood vessel puncture site is important for procedures such as percutaneous access to prevent bleeding and hematoma. Thus, a solution to facilitate hemostasis at a puncture site may be achieved by deploying a flexible hemostatic plug within the puncture tract.

Figure 1A:
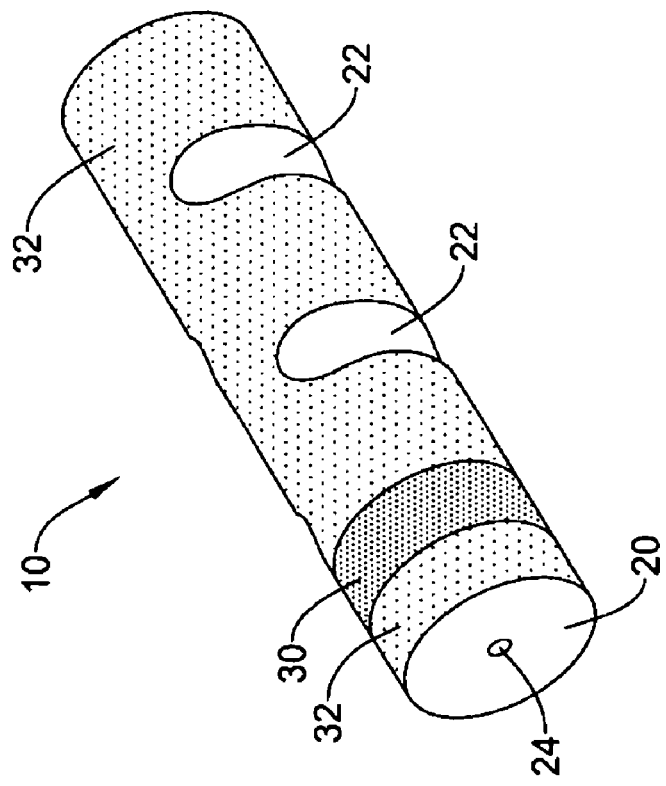
FIG. 1A is a perspective view of a composite arteriotomy closure plug of the invention.

Referring now to FIGS. 1A-B, which together illustrate a composite arteriotomy closure plug (10) having an elongate core member (20) provided with a lumen (24) extending axially from a distal end to a proximal end and sized to accept a suture (not shown), it will be seen that the core member has been provided with a first layer (30) and second layers (32). The core member may be formed from absorbable gelatin foam such as GELFOAM® (Pharmacia & Upjohn, Inc., Bridgewater, N.J.), Surgifoam™ (Johnson & Johnson, New Brunswick, N.J.), CURASPON® (CuraMedical BV, Assendelft, Netherlands), GELITASPON® (Gelita Medical BV, Amsterdam, Netherlands), GELASPON® (Juvalis-Bernburg, Germany), or similar materials which may become available.

Layers (30) and (32), which may be continuous or discontinuous and which may optionally overlap, may be formulated from materials including a hydrogel, a hemostatic material, an antimicrobial, a growth promoter, thrombus enhancing agents, and the like. It will also be appreciated that the layers may be discrete layers applied to the plug by, for example, extrusion or coating or may be present as generally surface regions of the plug which contain elevated amounts of the layer material. These regions of enriched material may be introduced by allowing the layer components to migrate into the plug material. The hydrogel component, if present, may include any of the commonly employed biocompatible hydrogels, such as polyethylene glycols (PEG) on the molecular weight range of about 600 to 6,000, including PEG 900, PEG 3350, and PEG 6000 (Sigma-Aldrich, St. Louis, Mo.). Of the hemostatic materials commonly available, starch such as BleedArrest™ Clotting Powder (Hemostasis, LLC, St. Paul, Minn.), PerClot™ (Starch Medical, San Jose, Calif.), SuperClot™ (Starch Medical, San Jose, Calif.) or Arista™ AH (Medafor, Minneapolis, Minn.) may be employed alone or in combination with polyethylene glycol as a binder. The hemostatic material may be mixed with the binder or may be adhered to the plug component(s) by contacting the plug component with the hemostatic material under conditions in which one or both have moistened surfaces. For example, a hydrogel material may be applied from solution by one of the common techniques such spraying and when the carrier has partially evaporated to a tacky state, the hemostatic material may be applied by impingement or by tumbling. In some embodiments, the hemostatic material may be applied directly to the plug where it may be mechanically retained within the pores of the foam. In addition to serving as a binder for a hemostatic material, the hydrogel component may also be used to modulate the rate of swelling of the gelatin foam and, in some embodiments, may serve as a lubricant during the deployment of the composite plug. The composite arteriotomy closure plug (10) of FIGS. 1A-B may optionally include horizontal or vertical slits, notches, grooves, helical grooves, and the like which are believed to facilitate axial compression of the plug and to provide controlled buckling and folding of the plug. Notches (22) are illustrated.

Figure 2B:
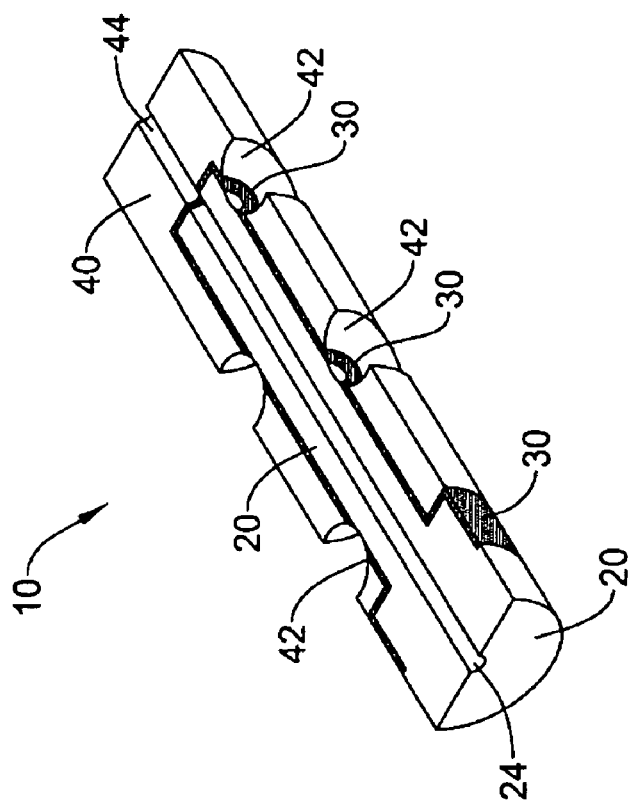
FIG. 2B is a perspective view of a longitudinally sectioned composite arteriotomy closure plug of FIG. 2A.
Figure 2A:
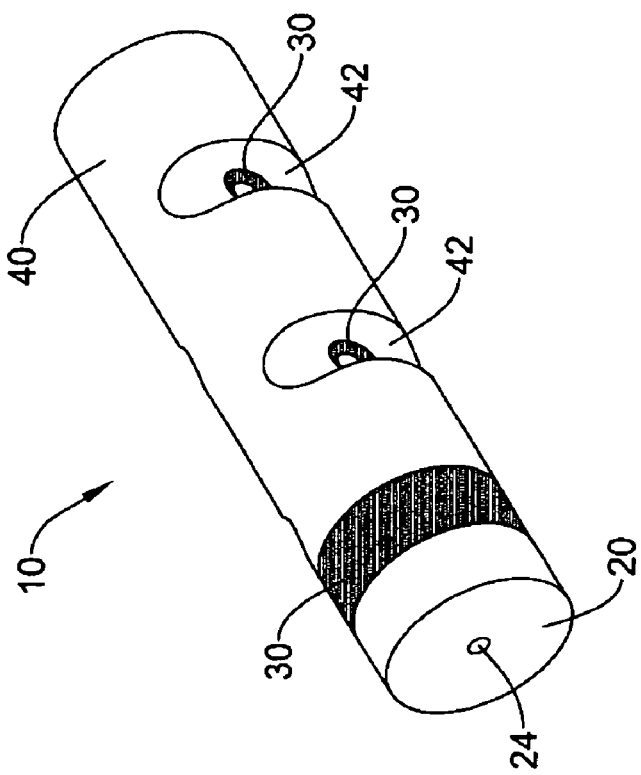
FIG. 2A is a perspective view of a composite arteriotomy closure plug of the invention.
Figure 3:
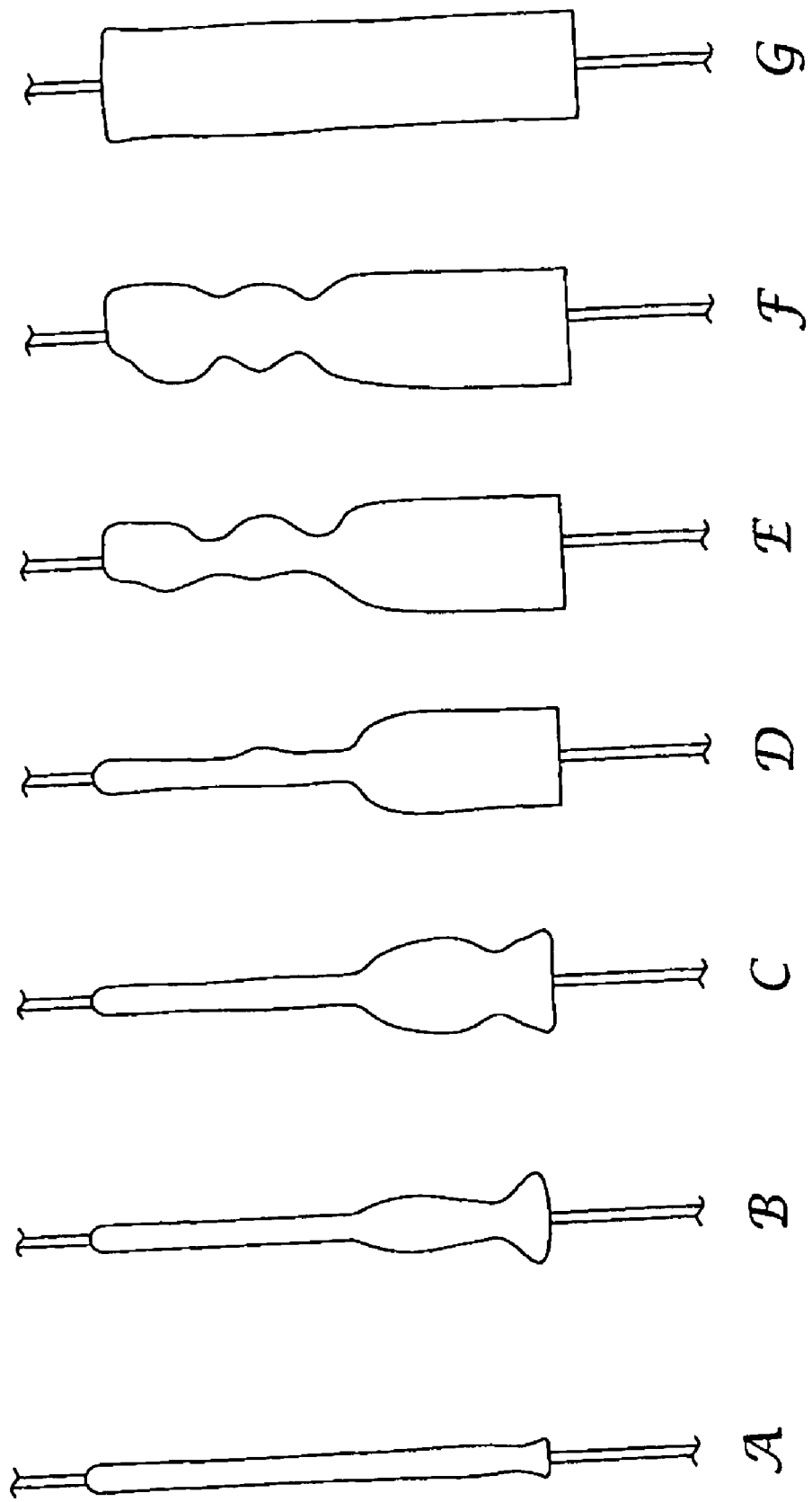
FIGS. 3A-G are schematic representations of stages in the expansion of a composite arteriotomy closure plug of the invention.

FIGS. 2A-B, which together illustrate a composite arteriotomy closure plug (10) having an elongate core member (20) provided with a lumen (24), additionally include an outer member (40) having the general shape of a cylindrical cap which mates with a core member (20) having a T-shaped axial cross-section resulting in a core member which resembles a cylindrical distal segment joined to a reduced diameter cylindrical proximal segment. The outer member (40) has at least a first lumen which may receive at least a portion of the core member and typically has a second lumen (44) sized and aligned with the lumen (24) of the core member to receive the suture (not shown) extending through the core member to provide a continuous path therefor. The exterior surfaces of the core member distal segment and the outer member proximal end may have substantially the same cross-section to provide a smooth join. As in the monolithic plug of FIGS. 1A-B, the plug of FIGS. 2A-B may optionally include horizontal or vertical slits, notches, grooves, helical grooves, and the like which are believed to facilitate axial compression of the plug and to provide controlled buckling and folding of the plug. Notches (42) are illustrated. Suitable modifications to control buckling of the composite plugs of this disclosure may be found, for example in co-pending applications Ser. No. 12/389,960, filed Feb. 20, 2009 and Ser. No. 12/389,847, filed Feb. 20, 2009, incorporated herein by reference in their entirety.

It will be appreciated that any given embodiment may have more than one core member and/or more than one outer member if desired. Such multi-component plugs may be useful in those configurations which would be difficult to fabricate from only one or two members. For example, distal and proximal outer members in the form of caps may be applied to a completely contained core member.

The layers associated with the closure plug of FIGS. 2A-B may have compositions similar to those discussed above. The layers may be positioned about the core member, between the core member and the outer member, and/or about the outer member. Although generally circumferential layers have bee depicted in FIGS. 1A through 2B, it will be appreciated that the layers may be applied as longitudinal stripes, as spirals, as patterned regions, and the like to achieve a swelling profile.

FIGS. 3A-G are illustrative of the progression in swelling which may occur when a composite arteriotomy closure plug is exposed to an appropriate fluid, in this case by full submersion in water. The radial expansion profile along the plug, as a function of time, may be altered by controlling the composition, placement, and thickness of layers applied to the plug and by the positioning of horizontal or vertical slits, notches, grooves, and the like. In addition, the profile may be controlled by mechanically altering the local porosity of the gelatin foam components. In some embodiments, it may be desirable to alter the expansion profile to favor early expansion near the distal end of the composite plug which is believed to stabilize the plug within the tract and to minimize proximal movement within the tract under the influence of any arterial blood pressure which may leak from the vessel. Additionally, it is believed that a swelling profile in which swelling is generally initiated at or near the distal end of the composite plug and continues at progressively more proximal locations may tend to press the composite plug distally into the tract to an extent which may resist ejection of the plug without undesirable intrusion into the vessel.

Figure 4:
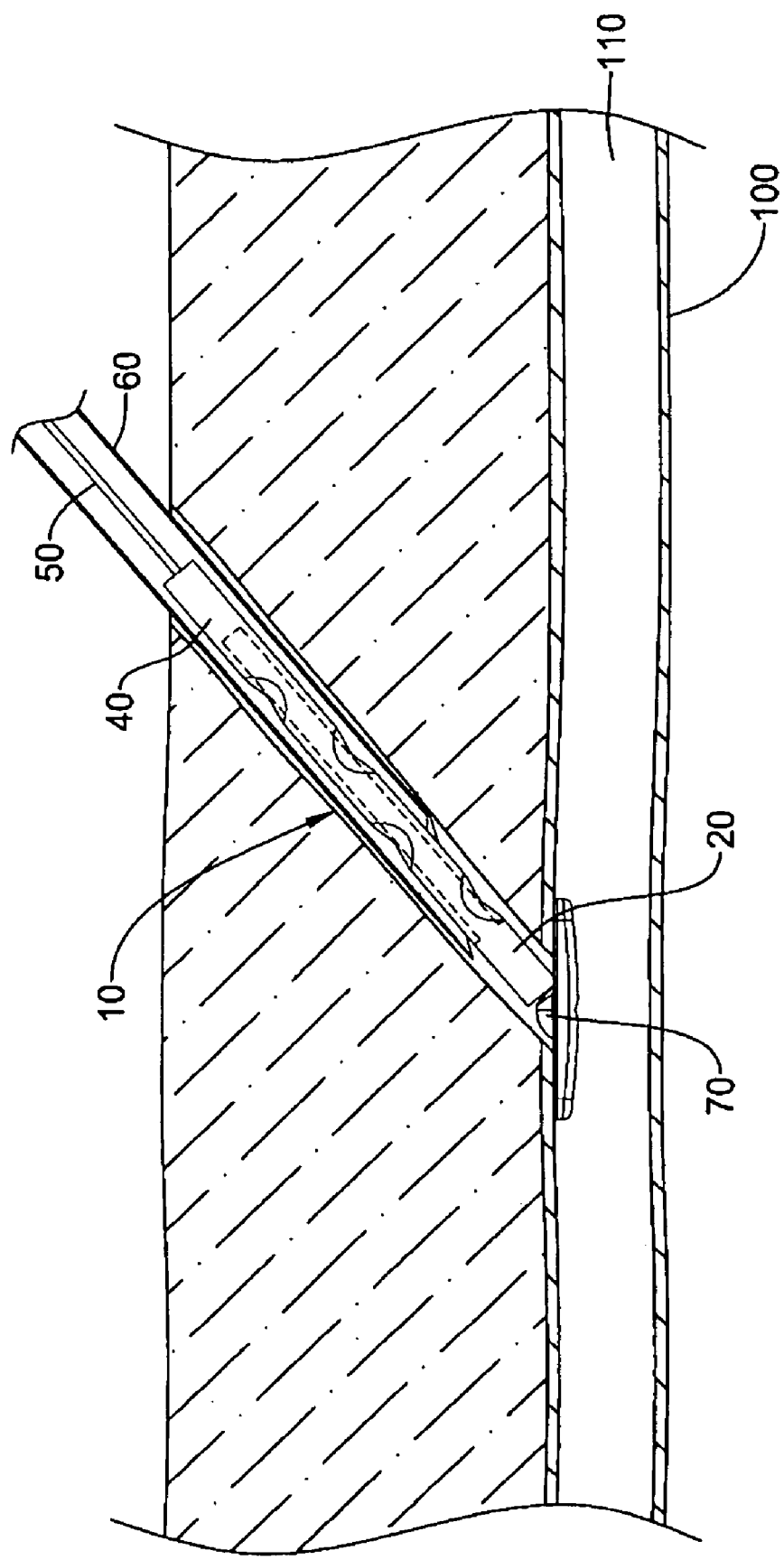
FIG. 4 is a schematic cross-section of a composite arteriotomy closure plug of the invention during delivery.

FIG. 4 illustrates schematically the deployment of a composite plug (10) for arteriotomy closure within a wound tract adjacent to an arterial puncture. The arterial wall (100) has been punctured proximate the anchoring site (70). In this illustrative example, an anchoring site for the suture (50) has been provided as a loop attached to a toggle or patch disposed within the lumen (110) of the artery although other anchoring site mechanisms are known and may be used with the composite arteriotomy closure plug. The composite plug (10) has been radially compressed within temporary sheath (60) and advanced through the tract to a position adjacent to the arterial puncture. As illustrated, the composite plug comprises a core member (20) and an outer member (40) which has been advanced along suture (50) to the deployment position. The composite plug (10) may then be ejected from the temporary sheath (60) by conventional means, which have been omitted for clarity, and the temporary sheath may be withdrawn, typically through a cannula within the wound tract. Following or concurrent with ejection, the composite plug may be axially compressed within the wound tract. A variety of techniques may be used alone or in combination. For example, the axial suture (50) may be placed in tension against a suture anchor site (70) while a slip knot is advanced distally along the suture. Compression may be augmented by the use of a pushrod. It is believed that the presence of horizontal or vertical slits, notches, grooves, helical grooves, and the like facilitate axial compression and folding in a controlled manner while minimizing forces which might tend to result in undesirable intrusion of the plug into the vessel. In other embodiments, the anchoring site may not need to provide a separate anchoring structure, but may simply provide sufficient fluid to create initial distal swelling of the composite plug which will serve to anchor the plug within the tract.

As noted above, in some embodiments one or more regions of the composite plug may be modified by horizontal or vertical slits or material may be removed to provide notches, grooves, helical grooves, and the like which may lower axial compression forces on the composite plug during deployment within a wound tract. Smooth compression is desirable to control buckling and folding of the composite plug while avoiding excessive internal stresses which may tend to allow the suture to tear the composite plug. In addition to facilitating compression, the removed regions may provide improved fluid access to the interior of the composite plug including, but not limited to, access to any interior layers which may be present therein.

In some embodiments, the layer or layers applied to components of the composite plug may provide a continuous layer which covers all or part of the surface of the plug. In other embodiments, the layers may be discontinuous as in longitudinal or circumferential stripes. When more than one layer is present on a surface, the layers may be spaced-apart, may abut, or may overlap. In addition to stripes or bands, the layers may be applied in a pattern-wise manner. One or more layers may be present between components of the composite plug. The layers associated with a composite plug may all have a similar composition or the composition may vary from layer to layer. In some embodiments, the composition of a single layer may vary along the length of the composite plug. In yet other embodiments a layer may comprise a region of higher concentration of layer material within a core member or outer member.

The components and placement of layers may be selected to enhance or to impede the uptake of fluid by the composite plug and so may be used to control the intermediate shapes which the composite plug adopts as it swells locally in response to fluid contact. For example, partially filling the surface structure of the gelatin foam with hydrogel, particularly a higher molecular weight hydrogel, will often impede uptake of fluid and so will delay the swelling of the composite plug locally. Conversely, lower molecular weight hydrogels may serve as wetting agents or surfactants and may enhance the uptake of fluids thereby accelerating swelling.

Although it is within the scope of the disclosure to apply the layers by any method known in the art, dip coating and spray coating have been found to be appropriate and convenient. The hydrogel has been applied from solutions in water, isopropanol, and ethanol. Alcoholic solutions of polyethylene glycol have been found to have little effect on the gelatin foam structure, while aqueous solutions, especially when used for dip coating, may partially collapse the foam structure near the surface. Polyethylene glycol applied to the gelatin foam prior to radial compression has been found to increase the volumetric expansion upon hydration. In some embodiments, it may be desirable to distribute polyethylene glycol, or other hydrogel material, throughout the gelatin foam by applying the hydrogel from an alcoholic solution by dip coating. The distribution of PEG within the foam may be controlled by varying the temperature and dip time. The resulting distribution may be essentially uniform or may gradually increase in concentration from the center toward the surface. Addition of suitable surfactants may increase the rate of penetration of PEG solutions through the gelatin foam. Drying of the plug following dip coating may be accomplished with or without the application of vacuum. The drying process may influence shrinkage and hydration volume expansion capacity without significantly affecting leak performance.

In addition to providing a layer comprising a material such as a hydrogel and/or hemostatic material on a portion of the surface of a core member and/or outer member, the surfaces of the composite plug may be further modified by local mechanical compression or elongation, partially collapsing the gelatin foam using heat, exposure of the surface to water followed by drying, or the like.

In some embodiments, in addition to a core member and layers thereon, the composite plug may include an outer member at least partially surrounding the core member. The outer member may be fabricated form the same gelatin foam as the core member, a gelatin foam having a different density, or a different material such as collagen. The outer member may have one or more lumens therethrough. One such lumen may be sized to receive a suture and generally aligned with the lumen of the core member when the core member and the outer member are assembled. An outer member lumen may be sized and positioned to accept at least a portion of the core member therein either before or after partial radial compression of that portion of the core member to be contained within the outer member.

In some embodiments, the core member will have a generally T-shaped axial cross-section and generally circular transverse cross-sections. An outer member for a core member having a generally T-shaped axial cross-section may have a mating generally U-shaped axial cross-section. In such embodiments, the cross-section of the enlarged distal end of the core member may be similar to the cross-section of the distal end of the outer member to provide a smooth transition between the two components. In other embodiments, the composite plug may comprise multiple core members and/or multiple outer members to facilitate fabrication of more complex composite plugs. It will be appreciated that transverse cross-sections of the core member(s) and the outer member(s) are not necessarily circular and that the overall shape of the composite plug is not necessarily cylindrical although those shapes may be somewhat easier to fabricate and have been selected for the nonlimiting illustrative examples. In some embodiments, the outer member may extend a short distance proximal of the proximal end of the core member. In these and other embodiments, the distal end of the core element may extend a short distance distal of the distal end of the outer element. Although the dimensions of the composite plug may be varied depending on anticipated usage sites, the length of the composite plug will often be greater than the average diameter of the plug and advantageously may be selected to be about four to five times the average diameter prior to radial compression although greater or lesser ratios may be employed.

In those embodiments which include at least one core member and at least one outer member, one or more layers including one or more of a hydrogel and a hemostatic material may be disposed between the at least one core member and at least one outer member. Although the layer or layers disposed between a core member and an outer layer usefully may tend to adhere the two components together, that is not a necessary function of the layer or layers. In those embodiments in which at least one layer is disposed between a core member and an outer member, any slits, notches, grooves, or the like which may be present may optionally expose or improve fluid access to a portion of the at least one layer. Optionally, the slits, notches, or grooves may penetrate the at least one layer.

The composite plug of the disclosure may be formed, for example, by removing excess gelatin foam from a blank larger than the desired core member and/or outer element. These components may then be provided with a lumen connecting the distal and proximal ends of the components, said lumen sized to receive a suture therethrough. If an outer member is to be used, the lumen thereof may be enlarged to accommodate at least a portion of the core member in a partially compressed or uncompressed state. At least one layer may be disposed about the components of the plug, said layer including at least one of a hydrogel and a hemostatic material. In some embodiments, the at least one layer may be applied to a core member. In other embodiments, the at least one layer may be applied to an outer member. In yet other embodiments, the at least one layer may be applied to both core members and outer members. The core member(s) and outer member(s) may be assembled by positioning at least a portion of the core member(s) within a lumen of a corresponding outer member or members with or without an interposed layer comprising a material including at least one of a hydrogel and a hemostatic material. A suture may be provided within the lumen of the core member(s) and may extend through lumens of any outer members which may be present thereby extending at least from the distal end of the composite plug to the proximal end of the composite plug. The assembled composite plug may then be provided with one or more horizontal or vertical slits, notches, grooves, helical grooves, or the like and at least partially compacted in a radial dimension. In some embodiments, a portion of the composite arteriotomy closure plug may be mechanically modified to alter the permeability of the plug to fluids. The mechanical modification may, for example, take the form of flexing the plug to partially break portions of the foam structure or of selectively piercing the plug to provide fluid access channels. Such modification may occur before or after application of one or more layers and before or after radial compression. Additional mechanical modification may occur after the formation of notches or grooves. The composite plug may be subjected to a drying or desiccating step to remove excess moisture prior to storage or use.

It is believed that the ability of the composite arteriotomy closure plug to seal a wound tract has at least two major contributors. The first is an enhanced ability to clot blood which may be attributed to contributions from both the gelatin foam and the hemostatic material. In addition to the clotting function, the gelatin foam, hemostatic material, and the hydrogel are each capable of swelling upon hydration to expand within the wound tract thereby closing any potential leak paths. Appropriately chosen hemostatic and hydrogel materials may also increase the viscosity of fluids within the tract further enhancing the sealing action. Although the relative amounts of the various components employed in a composite arteriotomy plug of the disclosure may vary with the particular materials selected, hydrogel loadings of 0 to about 3:1 and hemostatic material loadings of about 0.25:1 to about 3:1 by weight on the weight of the foam will often be appropriate.

As shown in FIGS. 3A-G, the localization of hydrogel and hemostatic material in layers, as well as mechanical modification of plug porosity, may be used to control the progression of swelling along the length of the disclosed composite closure plug to a degree not possible with a conventional arteriotomy closure plug which tends to swell uniformly upon exposure to bodily fluids. By initiating swelling near the distal end and delaying swelling near the proximal end, the plug may be provided with early stability within the wound tract, attributable to the soft wide base, while maintaining firmness for deliverability near the proximal end. As discussed above, progressive swelling from the distal end toward the proximal end of the plug is believed to resist expulsion of the plug under the influence of arterial blood pressure.

Testing of a variety of composite plugs of the disclosure versus unmodified gelatin foam plugs, as well as commercially available plugs, has shown a reduction in peak by-pass water flow rates within a simulated tract of the order of 3.5:1 to 28:1 in the initial minute of exposure. Further, unmodified gelatin foam plugs allowed sustained leakage during the second through the tenth minute of exposure which ranged between 10 and 16 ml/min compared to essentially zero leakage for composite plugs under the same test conditions. A commercially available collagen arteriotomy closure plug allowed sustained leakage of 3 to 4 ml/min under the same conditions.

Once fabricated and compressed, the composite arteriotomy closure plug may be inserted into a temporary containment sheath for delivery to the vicinity of the vessel puncture. Apparatus suitable for delivering the composite arteriotomy closure plug is disclosed in co-pending application Ser. No. 12/390,241, filed Feb. 20, 2009 incorporated herein by reference in its entirety. In some embodiments, the radial compression which accompanies insertion into a temporary containment sheath may be of the order of 3:1, 8:1, or even 10:1. A degree of elastic rebound may be expected. In some embodiments, the suture may be attached to an anchor adjacent to a vessel puncture. The anchor site may be any of the anchor sites known in the art. For example, it may take the form of a loop attached to a toggle or patch located within the punctured vessel. Other forms of anchor site are also contemplated. For example, the anchor site may be formed by the distal lip of a catheter, cannula, or the temporary sheath within which the composite plug is contained if the lip serves to position the suture extending from the distal end of the composite plug adjacent to the vessel puncture during the deployment of the composite plug. Following insertion of the temporary containment sheath within the wound tract and tensioning of the distal suture to ensure that the composite plug is properly positioned within the tract, the composite plug may be ejected from the temporary containment sheath and, if necessary, further oriented within the tract by manipulation of the proximal end of the plug as it begins to expand. In addition, the composite plug may be axially compressed with attendant buckling and or folding within the wound tract. In other embodiments, a suture may not be required for proper deployment of the composite plug and swelling of the distal end upon exposure to fluids may suffice to anchor the plug within the tract. The containment sheath, as well as any other apparatus remaining within the wound tract, may then be removed to allow the composite plug to expand and seal the tract.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A composite plug for arteriotomy closure comprising:
   an elongate core member having a distal end, a proximal end, and a lumen connecting the distal end and the proximal end, said lumen sized to receive a suture;
   one or more layers disposed at least in part about the core member; and
   an outer member at least partially surrounding the core member, said outer member having a distal end and a proximal end;
   wherein the core member comprises a gelatin foam and the one or more layers comprise a material selected from the group consisting of a hydrogel, a hemostatic material, and combinations thereof;
   wherein a portion of the core member extends distally with respect to the outer member;
   wherein distal of the one or more layers, a lateral cross-section of the composite plug includes only the elongate core member; and
   wherein proximal of the one or more layers, a lateral cross-section of the composite plug includes only the outer member.

2. The composite plug of claim 1, further comprising one or more regions in which a portion of the plug has been removed.

3. The composite plug of claim 2, wherein the one or more regions in which a portion of the plug has been removed is in the form of a notch.

4. The composite plug of claim 2, wherein the one or more regions in which a portion of the plug has been removed is in the form of a groove.

5. The composite plug of claim 1, wherein the core member has been modified by the inclusion of one or more slits.

6. The composite plug of claim 1, wherein the one or more layers are continuous.

7. The composite plug of claim 1, wherein the one or more layers are discontinuous.

8. The composite plug of claim 1, wherein the outer member comprises gelatin foam.

9. The composite plug of claim 1, wherein the outer member includes a lumen sized to receive a suture.

10. The composite plug of claim 9, wherein the lumen of the outer member is axially aligned with the lumen of the core member.

11. The composite plug of claim 1, wherein the outer member extends proximally with respect to the core member.

12. The composite plug of claim 1, wherein the distal end of the outer member and the portion of the core member which extends distally with respect to the outer member have substantially the same cross-section.

13. The composite plug of claim 1, wherein the one or more layers disposed about the core member are disposed at least in part between the core member and the outer member.

14. The composite plug of claim 13, wherein at least a portion of the one or more layers disposed about the core member are not covered by the outer member.

15. The composite plug of claim 1, wherein the outer member further comprises one or more layers comprising a material selected from the group consisting of a hydrogel, a hemostatic material, and combinations thereof.

16. The composite plug of claim 15, wherein the one or more layers of the outer member are continuous.

17. The composite plug of claim 15, wherein the one or more layers of the outer member are discontinuous.

18. The composite plug of claim 1, wherein the outer member further comprises a material selected from the group consisting of a hydrogel, a hemostatic material, and combinations thereof.

19. The composite plug of claim 1, wherein the outer member has been modified by the inclusion of one or more slits.

20. The composite plug of claim 1, wherein the core member further comprises a material selected from the group consisting of a hydrogel, a hemostatic material, and combinations thereof.

* * * * *